United States Patent
Lindhofer et al.

(10) Patent No.: US 9,605,242 B2
(45) Date of Patent: Mar. 28, 2017

(54) REMOVAL OF TUMOR CELLS FROM INTRAOPERATIVE AUTOLOGOUS BLOOD SALVAGE

(71) Applicant: Trion Pharma GmbH, Munich (DE)

(72) Inventors: Horst Lindhofer, Munich (DE); Michael Stroehlein, Köln (DE); Markus Heiss, Köln (DE)

(73) Assignee: Horst Lindhofer, Munich (DE)

( * ) Notice: Subject to any disclaimer, the term of this patent is extended or adjusted under 35 U.S.C. 154(b) by 0 days.

(21) Appl. No.: 14/349,898

(22) PCT Filed: Oct. 4, 2012

(86) PCT No.: PCT/EP2012/069584
§ 371 (c)(1),
(2) Date: Apr. 4, 2014

(87) PCT Pub. No.: WO2013/050445
PCT Pub. Date: Apr. 11, 2013

(65) Prior Publication Data
US 2014/0369985 A1 Dec. 18, 2014

(30) Foreign Application Priority Data
Oct. 4, 2011 (EP) ..................... 11183851

(51) Int. Cl.
A61K 35/14 (2015.01)
G01N 33/574 (2006.01)
C07K 16/30 (2006.01)
C12N 5/00 (2006.01)
C07K 16/28 (2006.01)
A61K 35/18 (2015.01)
C07K 16/46 (2006.01)
C12N 5/078 (2010.01)

(52) U.S. Cl.
CPC ............ *C12N 5/0093* (2013.01); *A61K 35/18* (2013.01); *C07K 16/2809* (2013.01); *C07K 16/30* (2013.01); *C07K 16/468* (2013.01); *C12N 5/0641* (2013.01); *C07K 2317/24* (2013.01); *C07K 2317/31* (2013.01); *C07K 2317/626* (2013.01)

(58) Field of Classification Search
CPC .............................. G01N 33/574; C07K 16/30
USPC ...................... 435/7.23; 530/387.3
See application file for complete search history.

(56) References Cited

U.S. PATENT DOCUMENTS

| | | | |
|---|---|---|---|
| 6,210,668 B1 | 4/2001 | Lindhofer et al. | |
| 6,551,592 B2 | 4/2003 | Lindhofer et al. | |
| 2010/0322933 A1* | 12/2010 | Lindhofer | C07K 16/2809 424/136.1 |
| 2011/0250287 A1* | 10/2011 | Bristow | A61M 1/3679 424/529 |

FOREIGN PATENT DOCUMENTS

EP 2 033 657 3/2009

OTHER PUBLICATIONS

Edmund A. M. Neugebauer (Jahresbericht 2010, Institut fur Forschung in der Operativen Medizin, Universitat Witten/Herdecke, Mar. 1, 2011, p. 1-98).*
Catling et al. (Anaesthesia, 2008, 63: 1332-1338).*
International Preliminary Report on Patentability corresponding to International Application No. PCT/EP2012/069584 dated Apr. 8, 2014.
International Search Report corresponding to International Application No. PCT/EP2012/069584 dated Jan. 23, 2013.
Riesenberg et al., "Lysis of Prostate Carcinoma Cells by Trifunctional Bispecific Antibodies (αEpCAM X α CD3)," The Journal of Histochemistry & Cytochemistry, vol. 49, No. 7, pp. 911-917 (2001).
Liumbruno et al., "Recommendations for the transfusion of red blood cells," Recommendations, Blood Transfus, 7:49-64 (2009).

* cited by examiner

*Primary Examiner* — Yan Xiao
(74) *Attorney, Agent, or Firm* — Jenkins, Wilson, Taylor & Hunt, P.A.

(57) ABSTRACT

The invention relates to a method performed ex vivo for removal of tumor cells from intraoperatively collected blood salvage, to antibodies and scaffold proteins which mimic antibodies for use in said ex vivo method, to the use of said ex vivo method for removal of tumor cells from intraoperatively collected blood salvage followed by reintroducing the so obtained purified blood salvage or of concentrates of erythrocytes purified by said method to a patient from whom said intra-operatively collected blood was obtained, as well as to blood salvage or a concentrate of erythrocytes, both obtainable by said method for reinfusion to said patient.

15 Claims, 3 Drawing Sheets

SEQUENCE LISTING

<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: Artificial linker sequence

<400> SEQUENCE: 1

Ser Ser Gly Gly Gly Gly Ser Asp Ile
1               5

REMOVAL OF TUMOR CELLS FROM INTRAOPERATIVE AUTOLOGOUS BLOOD SALVAGE

FIELD OF THE INVENTION

The invention relates to a method performed ex vivo for removal of tumor cells from intraoperatively collected blood salvage, to antibodies and scaffold proteins which mimic antibodies for use in said ex vivo method, to the use of said ex vivo method for removal of tumor cells from intraoperatively collected blood salvage followed by reintroducing the so obtained purified blood salvage or of concentrates of erythrocytes purified by said method to a patient from whom said intraoperatively collected blood was obtained, as well as to blood salvage or a concentrate of erythrocytes, both obtainable by said method for reinfusion to said patient.

BACKGROUND OF THE INVENTION

Since the AIDS epidemic of the early 1980s the interest in alternatives to allogeneic blood transfusion has grown, particularly for elective surgery. One alternative that currently accounts for over 5% of the blood donated in the United States and some countries in Europe is autologous transfusion, obtained primarily by preoperative donation. In addition to preoperative blood donation, intraoperative blood salvage (IBS) (Table 1) from the surgical field represents an important option for covering transfusion demands. Along this IBS process, blood lost by a surgical patient is collected, cleaned, and made available for reinfusion to that patient.

Briefly, blood shed into the surgical field is aspirated from this site into an especially designed containment. Citrate or heparin anticoagulant is added, and the contents are centrifuged and/or filtered to remove leukocytes and clots and debris. IBS devices used can vary from simple, inexpensive, sterile bottles filled with anticoagulant to expensive, sophisticated, high speed cell washing devices (e.g. Medtronic Sequestra 1000, Cobe BRAT 2, Medtronic Autolog, Haemonetics Cell Saver-5® and Fresenius CATS®; Bentzien et al., *Anaesthesist* 49: 505, 2000; Serrick et al., J. Extra Corpor. Technol. 35(1): 28, 2003; Carless et al., The Cochrane Review, In: The Cochrane Library, John Wiley & Sons, Ltd., issue 3 pp. 1-180, 2010). Used in close to a million surgeries each year in the USA, the IBS procedure has become an integral part of blood management and conservation programs of hospitals (www.bloodbook.com).

TABLE 1

Benchmarks of intraoperative blood salvage in cancer surgery

| | |
|---|---|
| Efficient blood saving | Relief of blood resources |
| Compatibility | Supply of blood |
| Rapid availability | Optimal therapy for blood loss |
| Cost-efficiency | Blood loss-dependent application |
| No excess of blood transfusion | After at least 1 L blood loss |
| Less deficiency in blood transfusion | Enhanced efficacy of chemo-/radiotherapy |
| High blood quality | Washed and fresh erythrocytes |
| Increased security | Reduced transfusion risks (e.g. infection, transfusion error, difficult cross-match) |
| No need for autologous pre-donation | Decrease costs of wasted units More practicable for clinicians |

Besides increased incidences of preoperative anemia, blood donation prior surgery raises serious additional economical questions due to the high overall transfusion rates (Carless et al., *Transfus. Med.* 14: 123, 2004). In addition, about 30% of preoperative autologous blood donations have to be discarded in Italy because not-required autologous blood products are excluded from allogeneic blood transfusions per se according to regulatory guidelines. In this regard IBS and subsequent autotransfusion generally represent safe and more cost-effective measures in blood management.

Advantages of Intraoperative Blood Salvage

In contrast to allogeneic red blood cell transfusions, IBS is considered a safe and efficacious alternative. Importantly, despite excellent viral diagnostics the risk of transferring HIV infection is 1 per 493.000 allogeneic blood transfusions, the risk of transferring hepatitis C virus infection is 1 per 103.000 and the risk of transmitting hepatitis B virus infection is 1 per 63.000 (Schreiber et al., *N. Engl. J. Med.* 334: 1685, 1996). Results of a 'Serious Hazards of Transfusions' study performed from 1996 until 2001 documented these risks of allogeneic transfusion incidences (Dzik et al., *Transfusion* 43: 1190, 2003). Strikingly, the transmission of infectious diseases by means of contaminated blood transfusions appears to be a minor risk compared to the enormous risks of ABO-incompatible blood due to administrative or human failure along the blood donation and transfusion process (Sazama, *Transfusion* 30: 583, 1990; Dzik et al., *Transfusion* 43: 1190, 2003). More than 70% of transfusion incidences could be attributed to incorrect transfused blood components mainly caused by administration failure and errors in sampling, prescription as well as in component collection (Dzik et al., *Transfusion* 43: 1190, 2003). Pre- and intraoperative autotransfusion of red blood cells bypasses per se these inherent risks of allogeneic blood transfusion. In general, autologous blood salvage techniques offer advantages but do not require infusions of crystalloid or colloid to preserve blood volume (Table 1). Many liters of blood can be salvaged intraoperatively during extensive bleeding, far more than with other autologous techniques.

Suitability of Patients for IBS

Intraoperative blood salvage has been available for over 25 years. It is used extensively in cardiothoriac surgery, vascular and trauma surgery, as well as liver transplantation. Contraindications to its use are bacterial infections and tumor cells probably shed into the blood of the surgery field, and use of microfibrillar collagen or other foreign material at the operative site. Nowadays, due to shortages of donor blood and fears of transmitted infections the use of IBS also gains great interest in cancer surgery with high blood loss. The reluctance of surgeons to use autotransfusion in cancer surgery has diminished, as reports found no increase in local recurrence or metastatic disease when compared with standard survival data (Klimberg et al., *Arch. Surg.* 212: 1326, 1986; Perseghin et al., *Vox Sang.* 72: 221, 1997). As reviewed by Vanderlinde et al. (*BMJ* 324: 772, 2002) red blood cell autotransfusions collected from preoperative blood donations could significantly lead to reduced infection and recurrence incidences during colorectal cancer surgery as compared to allogeneic transfusions (Table 2). Some of these reviewed clinical trials are even more important as colorectal surgeries have been per se excluded from IBS recommendations due to the inherent risk of transmitting bacterial infections.

TABLE 2

Clinical outcome of randomized trials of autologous versus allogeneic transfusion*

| Study | No of patients | Type of surgery | Intervention | Type of complication | % of cases developing complications after transfusion | | P value for reduction in postoperative complications |
|---|---|---|---|---|---|---|---|
| | | | | | Autologous | Allogeneic | |
| Busch et al, 1993[9] | 423 | Colorectal | Predeposit autologous donation | Infection | 27 | 25 | NS |
| *N. Engl. J. Med.* 328: 1372, 1993 | | | | Recurrence | 37 | 34 | NS |
| Heiss et al, 1993 and 1994[10, 14] | 120 | Colorectal | Predeposit autologous donation | Infection | 12 | 27 | <0.05 |
| *Lancet* 342: 1328, 1993 *J. Clin. Oncol.* 12: 1859, 1994 | | | | Recurrence | 17 | 29 | 0.11 |
| Newman et al, 1997[11] | 70 | Knee replacement | Postoperative autologous salvage | Infection | 6 | 34 | <0.05 |
| *J. Bone Joint Surg. Br.* 79: 630, 1997 | | | | | | | |
| Farrer et al, 1997[12] | 50 | Vascular | Postoperative autologous salvage | Infection | 13 | 44 | 0.029 |
| *J. Vasc. Nurs.* 15: 111, 1997 | | | | | | | |
| Thomas et al. 2001[13] | 231 | Knee replacement | Postoperative autologous salvage | Infection | NA | NA | 0.036 |
| *Br. J. Anaesth* 86: 669, 2001 | | | | Readmission | NA | NA | 0.008 |

NS = not significant
NA = not available (ie not reported).
*Table is taken from Vanderlinde et al., *BMJ* 324: 772, 2002.

Nevertheless, a study clearly showed that tumor cells were detectable in the surgery field, although their impact on cancer recurrence remained unclear (Hansen et al., *Arch. Surg.* 130: 387, 1995). For instance the number of tumor cells in the peripheral blood and IBS of 61 patients with cancer surgery of an abdominal, orthopedic, urological, gynecological, or head and neck malignant tumor were compared. In 57 of 61 patients tumor cells were detected in the blood shed during oncological surgery. These tumor cells were identified by proliferation capacity, invasiveness, and tumorigenicity with a sensitivity of 10 tumor cells per 500 mL blood (Hansen et al., *Arch. Surg.* 130: 387, 1995). Interestingly, the number of tumor cells in the shed blood did not correlate with the amount of blood loss and only in 26% of these patients circulating tumor cells could be detected in the peripheral blood. Therefore, it is estimated that the number of tumor cells in the blood shed into the surgery field could range from 10 to $10^7$. These results were also confirmed independently by Dale et al., *Br. J. Surg.* 75: 581, 1988 and Müller et al., *Anaesthesist* 45: 834, 1996.

To further address safety concerns about the risk of residual tumor cells in IBS samples, additional approaches are needed to effectively eliminate the contaminating tumor cells:

One method used in combination with automatic IBS devices like Cell Saver-5® is represented by additional filtration of samples through leukocytes depletion filters (e.g. Pall RC400, RCEZ1T), RC XL-1) (Bontadini et al., *Transfusion* 34. 531, 1994; Yaprak et al., *Turk. J. Pediatr.* 40: 89, 1998; Gwak et al., *Liver Transplant.* 11: 331, 2005). The safe transfusion of erythrocytes collected by IBS does not impair clinical outcome as evaluated in several trials (Edelman et al. *Urology* 47: 179, 1996; Perseghin et al., *Vox Sang.* 72: 221, 1996; Davis et al., *BJU International* 91: 474, 2003).

In a different IBS approach the samples are irradiated at 50 Gy due to the underlying principle of radiosensitivity of nucleated cancer cells and due to the radioresistance of non-nucleated red blood cells.

Due to the complex logistic demand of this IBS/irradiation approach including additional staff requirement, dosimetry issues, suitable as well as certified irradiation equipment in the clinical department, this latter procedure is not in favor of broad application. In contrast, the filtration procedure for leukocyte depletion represents an elegant approach to reduce residual tumor cells during IBS although this technique still has the inherent risk of residual tumor cells still passing the filter.

Problems to be Solved by the Present Invention

Therefore, for further enhanced safety in cancer surgery to remove residual tumor cells, all known methods for reintroducing autologous blood obtained e.g. during surgery from wounds of patients with tumors have to be improved in order to provide a reliable removal of possibly contaminating tumor cells; said improvement should be capable of being easily implemented in e.g. devices like Cell Saver-5® or CATS® or into any other methods to reintroduce blood from patients who had undergone surgery.

SUMMARY OF THE INVENTION

The novel approach found by the present inventors is based on antibody-mediated formation of multi-cellular complexes, i.e. associates, comprising tumor cells recognized by antibody-driven tumor-associated antigen recognition, and optionally further by recognition of immune cells (leukocytes) like T cells and Fc-receptor positive accessory cells and/or further tumor cells followed by removal of said associates by e.g. centrifugation and/or filtration steps. Instead of or in combination with antibodies also protein scaffolds which mimic antibodies can be used.

BRIEF DESCRIPTION OF THE FIGURES

The invention will be illustrated in more detail also by means of the accompanying figures. The figures show.

DETAILED DESCRIPTION OF THE INVENTION AND PREFERRED EMBODIMENTS

The following discussion is included for purposes of describing the present invention and illustrating preferred embodiments thereof and is not intended to be limiting the scope of the specific methods, uses and compositions disclosed.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of the present disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

The present invention concerns an ex vivo-method for
  removal of tumor cells from intra-operatively obtained blood salvage comprising the following steps:
  providing intra-operatively obtained blood salvage;
  contacting said intra-operatively blood salvage with
    at least one antibody selected from the group consisting of a bispecific, trispecific, tetraspecific and multispecific antibody, each antibody having monovalent, bivalent, trivalent, tetravalent or multivalent binding properties, and/or
    with at least a scaffold protein which mimics a bispecific, trispecific, tetraspecific or multispecific antibody and having monovalent, bivalent, trivalent, tetravalent or multivalent binding properties,
  wherein the at least one antibody and/or the at least one scaffold protein is contacted with said intra-operatively obtained blood salvage for a time period which is sufficient to cross-link tumor cells and optionally immune cells and/or other tumor cells in order to obtain associates, wherein said tumor cells, said other tumor cells and said immune cells are potentially present in the intra-operatively obtained blood salvage, and wherein said tumor cells are specifically recognized by said at least one antibody or said at least one scaffold protein; and
  removing said associates from said intra-operatively obtained blood salvage.

Other preferred embodiments are described in the following description and the examples in combination with the figures. Further preferred features of the invention can be taken from the claims.

The presently described method is practiced ex vivo, i.e. outside the human body. Intra-operative blood salvage (IBS) is well known in the art and is also described as "autologous blood salvage". Blood which is lost during surgery is recovered and re-infused into the same patient from whom the blood lost during surgery has been gained.

The presently described method is directed to the removal of tumor cells which potentially might contaminate intra-operatively obtained blood salvage. The blood is obtained from patients who undergo a surgery treatment and suffer from tumors or who are suspected to harbor cells which might be considered to be tumorigenic.

Generally, the method starts with the surgeon aspirating blood from the surgical field. The collecting step is generally performed via a suction device. The aspirated blood is then mixed with an anticoagulant in order to avoid coagulation of the blood. The aspirated blood is collected in a reservoir until there is sufficient blood for processing.

Reference to an "anti-coagulant" includes classes of anti-coagulants such as anticoagulants, anti-platelet drugs, thrombolytic and fibrinolytic drugs and metal ion chelators agents such as e.g. citrate, citrate dextrose (ACD) and EDTA and oxalate. In a related aspect, the anti-coagulants include heparin and glycosaminoglycans such as low molecular weight heparin such as Bemiparin, Certoparin, Dalteparin, Enoxaparin, Nadroparin, Pamaparin, Reviparin and Tinzaparin and heparinoid such as Danaparoid, Sulodexide, Dermatan sulfate; direct thrombin (II) inhibitors such as Argatroban, Bivalirudin, Dabigatran, Desirudin, Hirudin, Lepirudin, Melagatran, Ximelagatran; Fact. Xa inhibitors (such as Tick Anticoagulant Peptide), such as Apixaban, Otamixaban, Rivaroxaban and oligosaccharides such as Fondaparinux and Idraparinux; Vitamin K antagonists such as Acenocoumarol, Clorindione, Coumatetralyl, Dicoumarol (Dicumarol), Diphenadione, Ethyl biscoumacetate, Phenprocoumon, Phenindione, Tioclomarol and Warfarin.

In one embodiment of the present invention, the so collected blood salvage might be tested on the presence of tumor cells wherein particularly preferred the type of tumor-associated antigen is determined by well-known methods in the art, e.g. by labeled antibodies specifically reacting with epitopes of tumor-associated antigens in order to determine the type tumor-antigen to which said antibody binds and which is to be applied in the invention.

Examples of tumors included in the present invention (but not limited thereto) comprise sarcomas and carcinomas, including fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyrgioma, ependymoma, pinealoma, hemangioblastoma, acoustic neuroma, oligodendroglioma, meningioma, melanoma, neuroblastoma and retinoblastoma). Further examples include epithelial tumors, hematological tumor and neuroectodermal tumors.

The intra-operative blood salvage is then contacted with an antibody or an appropriate protein scaffold which is capable of specifically detecting at least one epitope of at least one tumor-associated antigen of at least one tumor cell.

As a further requirement, said antibody must be capable of forming a network of at least said antibodies and said tumor cells in order to obtain aggregates or associates consisting of said antibodies and tumor cells. In a further particularly preferred embodiment of the present invention, said antibody is also capable of binding to other tumor cells and/or to immune cells in order to form a three-dimensional network of antibodies and tumor cells and optionally immune cells and further optionally or additionally other tumor cells. Due to the composition, structure and size of said associates resulting from the formation of multi-cellular complexes, the associates are capable of being removed from said IBS by centrifugation or filtration or a combination thereof. It is to be understood that filtration and centrifugation are preferred methods while other methods in order to efficiently remove said associates comprising residual tumor cells might be recognized by the person skilled in the art.

The invention therefore focuses on the mechanical removal of associates and aggregates formed by associating and aggregating antibodies and antibody-like molecules with tumor-associated antigens on tumor cells and optionally immune cells and/or other tumor cells and not on the depletion of tumor cells carrying tumor-associated antigens by destruction of said tumor cells by antibody-specific interactions and immunological effects. While using antibodies in a conventional way as immunological agents in order to destroy tumor cells by interacting with immune cells, the invention gains benefit only on the antibodies' or scaffold proteins' capacity of being capable in crosslinking antigens which are in the present case located on tumor cells or fragments thereof. The effects of the invention are achieved and consist therefore only on the interaction of the antibodies or antibody-like molecules with said tumor cells and removal of said three-dimensional network by centrifugal and/or filtration separation methods.

While in methods known in the art antibodies or antibody-like molecules may be linked to magnetic components like magnetic beads or other structural elements which facilitate removal of antibody complexes via said structural elements, or tumor cells are removed by cell sorting methods like flow cytometry, these embodiments are excluded from the present invention. Only due to the formation of a 3-dimensional network of antibodies and antibody-like molecules like scaffold proteins with antigens like tumor-associated antigens on tumor cells or fragments thereof, and optionally immune cells and/or other tumor cells, a mechanical removal of said associates is possible. Hence the antibody or the scaffold protein is not associated with any other structural components like magnetic beads or fluorescent molecules which might facilitate said removal.

While the present invention is herein described specifically with respect to trifunctional bispecific antibodies, particularly with respect to the trifunctional bispecific antibody catumaxomab which is directed against tumor-associated antigen EpCAM, and which is additionally binding to a T cell via CD3 and to Fc-receptor positive cells by its Fc-portion, the present invention is not limited to said specific embodiment. The specific embodiments described in the examples have to be understood as exemplary embodiments which provide evidence for the feasibility of the present invention. Having provided evidence on the excellent removal of tumor cells from IBS by catumaxumab, proof of concept has been given for the principle the presently claimed method is based upon. Having provided this evidence, the person skilled in the art will inevitably have the possibility to expand the concept to other tumors and other antibodies which are able to interact with said tumor cells and said immune cells in order to provide for a three-dimensional network, i.e. multi-cellular complexes which can be removed for instance by centrifugation and/or filtration.

The antibodies of the present invention are specifically selected from the group consisting of a bispecific, trispecific, tetraspecific or a multispecific antibody. A bispecific antibody is defined as an antibody capable of binding to two different type of antigens; a trispecific antibody is characterized by binding to three different types of antigens; a tetraspecific antibody is characterized by binding to four different types of antigens while a multispecific antibody is defined as being capable of binding multiple different types of antigens. Bispecific antibody catumaxumab is defined by binding to the tumor-associated antigen EpCAM on the one hand and to CD3 of a T cell on the other hand as well as with accessory cells by its Fc part.

The bi-, tri-, tetra- and multispecific antibodies described above may be monovalent, divalent, trivalent, tetravalent or multivalent. An antibody with a monovalent binding property is defined as an antibody which is capable of binding to one tumor-associated antigen. A bivalent monoclonal antibody is defined as an antibody which is capable of binding to two tumor-associated antigens or one tumor-associated antigen and one immune cell-associated antigen. A trivalent monoclonal antibody is defined as an antibody which is capable of binding to three different tumor-associated antigens or two tumor-associated antigens and one immune cell-associated antigen or one tumor-associated antigen and two immune cell-associated antigens. A tetravalent monoclonal antibody is defined as an antibody which is capable of binding to four different tumor-associated antigens or two different tumor-associated antigens—each having two identical antigen binding arms—or two/three tumor-associated antigens and one immune cell-associated antigen or two tumor-associated antigens and two immune cell-associated antigens. A multivalent monoclonal antibody is defined as an antibody which is capable of binding to one or more tumor-associated antigens and/or one or more immune cell associated antigen. The term "binding to a tumor-associated antigen" is defined as binding to an epitope of said tumor-associated antigen on a tumor cell.

Examples of antibodies which can be used in accordance with the present invention are described by Kontermann R E (ed.), Springer Heidelberg Dordrecht London New York, pp. 1-28 (2011) having bispecific or trispecific (trifunctional) formats with bivalent, trivalent and tetravalent binding properties to one tumor-associated antigen and to one or more surface antigens of leukocytes (i.e. cells of the immune system) are of importance for this patent application.

Bispecific antibody formats with bivalent antigen binding features:
    e.g. scFv (e.g. BiTE class), Db, scDb, dsDb, DART, dAb$_2$/VHH$_2$, knob-into-holes derivates, SEED-IgG, heteroFc-scfv, Fab-scFv, CrossMabs Bi-(tri-)specific antibody formats with trivalent antigen binding features:
    e.g. triple body, DNL-F(ab)$_3$, scFv$_{2-CH1/CL}$, dAb$_3$, Fab-scFv$_2$, IgG-scFab Bi-(tri-)specific antibody formats with tetravalent antigen binding features:
    e.g. IgG-scFv, scFv-IgG, scFv-Fc, F(ab')$_2$-scFv$_2$, sDb-Fc, scDb-C$_H$3, Db-Fc, scFv$_2$-H/L, DVD-Ig, tandAb, scFv-dhlx-scFv, dAb$_2$-IgG, two-in-one mAb, mAb$^2$, dAb-IgG, dAb-Fc-dAb.

Figure 2:
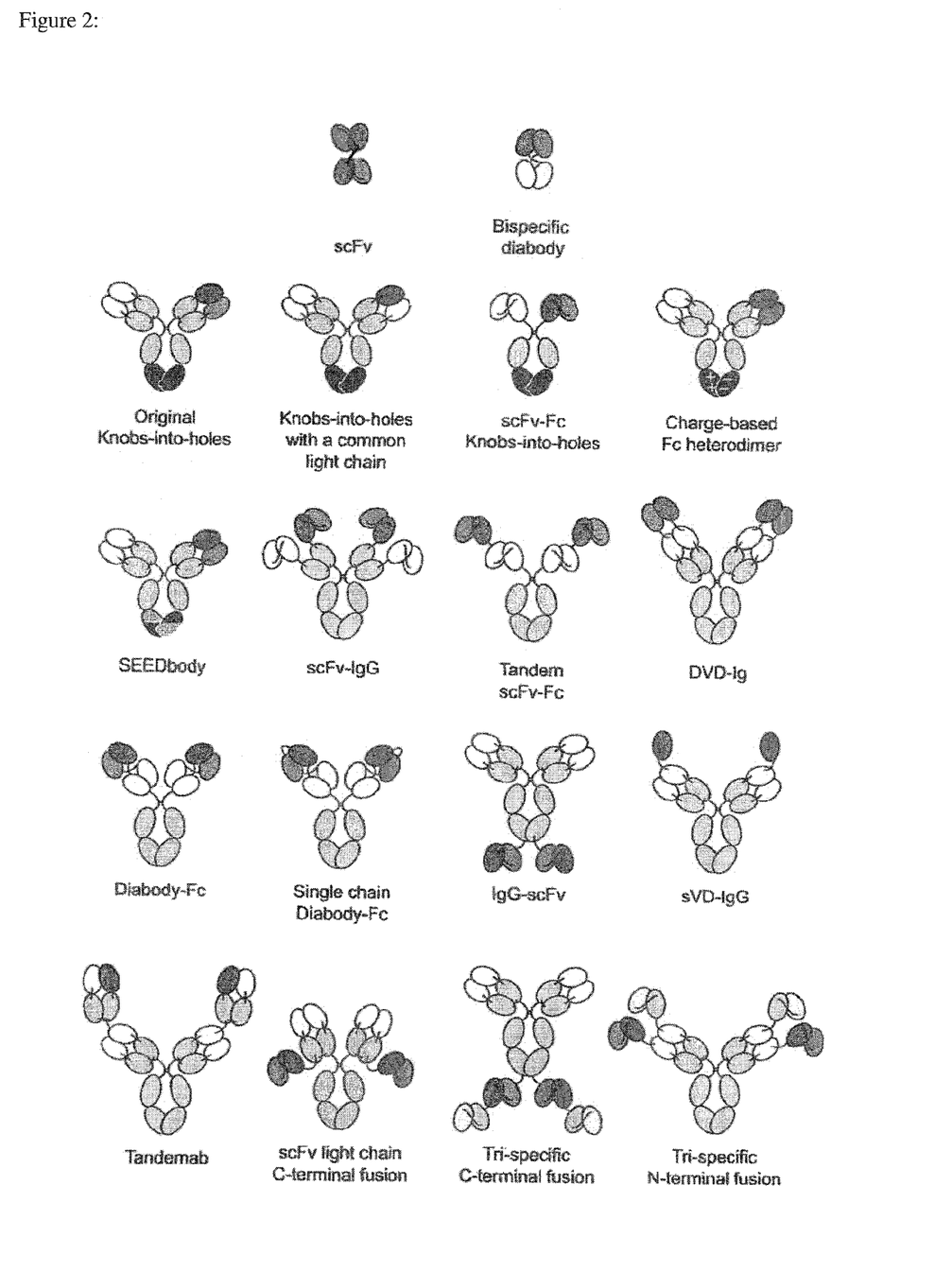
FIG. 2: Schematic drawings of representative antibody formats that have the capacity to form multicellular complexes consisting of tumor cells and peripheral blood leukocytes (i.e. immune cells). Drawings are taken from Jin P and Z Zhu. In: Bispecific Antibodies. Kontermann R E (ed.), Springer Heidelberg Dordrecht London New York, pp. 151-170 (2011) and have been slightly modified.
Figure 3:
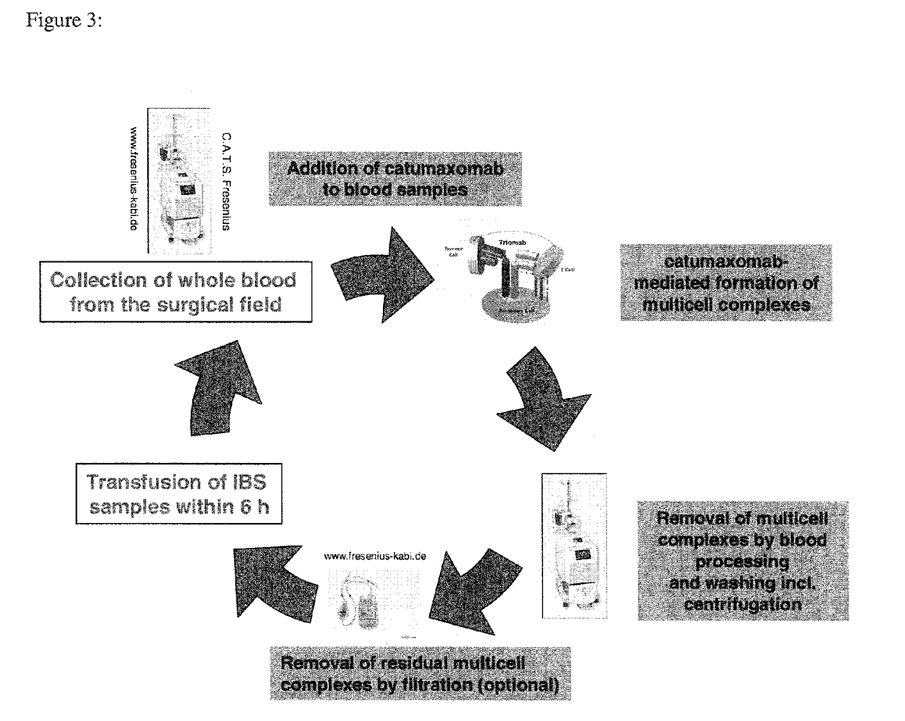
FIG. 3: Exemplary embodiment of a method of the invention using catumaxomab

Further examples of antibodies falling under the scope of the present invention are shown in the enclosed FIG. 2.

Additional antibodies falling under the scope of the present invention are described in the following references:

Müller D and R E Kontermann. In: Bispecific Antibodies. Kontermann R E (ed.), Springer Heidelberg Dordrecht London New York, pp. 83-100 (2011)
scFv (BiTE)

Baeuerle P A, Zugmaier G and D Rüttinger. In: Bispecific Antibodies. Kontermann R E (ed.), Springer Heidelberg Dordrecht London New York, pp. 273-288 (2011)
DVD-Ig Tarcsa E, Fraunhofer W, Ghayur T, Salfeld J and J Gu. In: Bispecific Antibodies. Kontermann R E (ed.), Springer Heidelberg Dordrecht London New York, pp. 171-186 (2011)
DNL-derivatives Chang C-H, Rossi E A, Sharkey R M, D M Goldenberg. In: Bispecific Antibodies. Kontermann R E (ed.), Springer Heidelberg Dordrecht London New York, pp. 199-216 (2011)
Two-in-One Antibodies Koeing P and G Fuh. In: Bispecific Antibodies. Kontermann R E (ed.), Springer Heidelberg Dordrecht London New York, pp. 187-198 (2011)
CrossMabs Schaefer et al. Proc. Natl. Acad. Sci. USA 108: 11187 (2011)

In a preferred embodiment, the antibodies used in the present invention are monoclonal antibodies. This is specifically true for the trifunctional bispecific antibodies described herein in detail.

Proteins having relatively defined three-dimensional structures are commonly referred to as protein scaffolds. These protein scaffolds may be used as reagents for the design of artificially engineered antibodies. These scaffolds typically contain one ore more regions which are amenable to specific or random sequence variation, and such sequence randomization is often carried out to produce libraries of proteins from which the desired antibody scaffolds may be selected. Such scaffolds are particularly useful in the field of antibody design.

These antibody scaffolds are non-immunoglobulin proteins which mimic properties of a monoclonal antibody with respect to its binding activity to for instance tumor cells and immune cells. Scaffolds often include loops or domains which form the binding side of said antibody scaffold. These antibody mimics may be utilized for the purpose of designing proteins which are capable of binding to virtually any compound of interest. This directed evolution approach results in the production of antibody-like molecules with high affinities for antigens of interest. In addition, those scaffolds may be used to display defined exposed loops (e.g. loops previously randomized and selected on the basis of antigen binding) in order to direct evolution of molecules that bind to such introduced loops. Methods on how to obtain antibody-like scaffold proteins are known in the art.

The following describes one possible approach for obtaining an antibody-like scaffold protein.

A first screening method, useful for the isolation or identification of randomized or mutated proteins of interest, involves: (a) contacting a compound of interest with a candidate protein, the candidate protein being a derivative non-antibody protein including a domain having an immunoglobulin-like fold, the non-antibody protein deriving from a reference protein by having a mutated amino acid sequence wherein the non-antibody protein binds with a Kd at least as tight as 1 microM to a compound that is not bound as tightly by the reference protein, wherein the contacting is carried out under conditions that allow compound-protein complex formation; and (b) obtaining, from the complex, the derivative protein that binds to the compound.

The second screening method is for isolating or identifying a compound which binds to a tumor-associated protein of interest. This method begins with a non-antibody protein including a domain having an immunoglobulin-like fold and deriving from a reference protein by having a mutated amino acid sequence, wherein the non-antibody protein binds with a Kd at least as tight as 1 microM to a compound that is not bound as tightly by the reference protein. This derivative protein is then contacted with a candidate compound (tumor-associated antigen or an epitope thereof), wherein the contacting is carried out under conditions that allow compound-protein complex formation, and the compound which binds to the derivative protein is obtained from the complex. Again, this general technique may be carried out with any protein.

Further methods of obtaining non-antibody proteins which bind to compounds of interest (tumor-associated antigen or an epitope thereof) are described as follows. One such method involves: (a) providing a non-antibody scaffold protein including an immunoglobulin-like fold, wherein the scaffold protein does not bind to the compound with a Kd as tight as 1 micro M; (b) generating mutated derivatives of the non-antibody scaffold protein, thereby producing a library of mutated proteins; (c) contacting the library with the compound; (d) selecting from the library at least one derivative protein which binds to the compound with a Kd at least as tight as 1 microM; and (e) optionally repeating steps (b)-(d) substituting for the non-antibody scaffold protein in repeated step (b) the product from the previous step (d). Again, this general technique may be carried out with any protein.

The so produced scaffold proteins mimic the function of an antibody as described above and below and can be used either instead of an immunoglobulin-based antibody or in combination with it.

The following describes in more detail trifunctional bispecific and trispecific antibodies which are used in an preferred embodiment of the invention. Once again it is emphasized that the invention is not intended to be restricted to these preferred embodiments as the concept of the invention is much broader. Further it is to be noted that the trifunctional bispecific and trispecific antibodies are herein described also with regard to their mode of action in the human body in order to provide for a full definition of these monoclonal antibodies. However, these intrinsic properties of said trifunctional bispecific and trispecific antibodies have no effect in the presently claimed invention as the antibodies are removed from the IBS almost completely, at least up to a non-detectable extent so that they do not provide any mode of action in the human body after reinfusion of the tumor cells depleted IBS. Specifically the presently described method is performed in vitro outside the human body so that any intrinsic biological activity of the antibodies cannot occur. Nevertheless it is believed that a description of the role these antibodies may play in vivo should be provided for a complete disclosure.

The trifunctional antibodies to be used in a preferred embodiment of the present invention are known in the art and are described in several documents. Reference is made e.g. to U.S. Pat. No. 6,551,592, US2003223999, US2002051780, and U.S. Pat. No. 6,210,668 and the articles indicated above; all of these documents and the following references are fully incorporated by reference into this application.

The antibodies to be used in the present invention are preferably characterized by the additional effects of
- activation of the Fc receptor-positive cell by binding to the Fc receptor-positive cell via Fcγ receptors of type I, IIa and III (CD64 and CD16) (18) and, thereby, initiating or increasing the expression of cytokines and/or costimulatory antigens; and
- transfer of at least a second activation signal, required for physiological activation of the T cell, to the T cell by the co-stimulatory antigens and/or cytokines, this activation being indicated by up-regulation of activation markers, killing of the tumor cell, and/or T cell proliferation.

Preferably, the antibodies used in the method and composition of the present invention are also able to activate tumor-specific T cells recognizing a tumor-specific peptide presented on the tumor cells by MHC class I and/or class II via their T cell receptor upon binding to the trifunctional bispecific or trispecific antibody as described herein.

Binding to the T cell takes place via CD3, CD2, CD5, CD28, and/or CD44. The Fc receptor-positive cells have at least one Fcγ receptor I, IIa or III.

The antibody used according to the invention is able to bind to monocytes, macrophages, dendritic cells, natural killer cells, neutrophils and/or eosinophilic cells being Fcγ receptor positive cells.

The antibodies used according to the invention lead to the initiation or increase of the expression of CD40, CD80, CD86, ICAM-1, and/or LFA-3 being co-stimulatory antigens and/or secretion of cytokines by the Fc receptor-positive cell. Preferably, the cytokines are IL-1, IL-2, Preferably, binding to the T cell takes place via the T cell receptor complex of the T-cell. said at least one trifunctional bispecific antibody recognizes a surface marker of T cells selected from the group consisting of CD3, CD2, CD4, CD5, CD6, CD6, CD8 and CD28.

Said tumor associated antigen the antibody or scaffold protein, preferably trifunctional bispecific antibody binds to is selected from the group consisting of: EpCAM, Her2neu, EGFR, CD30, CD20, CD22, MUC1, MUC1*, PSMA, CD33, MCSP, cMet, EphA2, Endosialin, Carboanhydrase IX, IGF-1R, FAP-alpha, CD19, CD52, GD2, CEA, FR, proteoglycans, G250, GC182, GT468, GT512.

The trifunctional bispecific antibody used in the invention preferably is an anti-CD3 X anti-tumor-associated antigen antibody and/or anti-CD2 X anti-tumor-associated antigen antibody and/or anti-CD5 X anti-tumor-associated antigen antibody and/or anti-CD28 X anti-tumor-associated antigen antibody and/or anti-CD44 X anti-tumor-associated antigen antibody.

The trispecific antibody preferably used according to the invention is an anti-CD3 X anti-tumor-associated antigen antibody and/or anti-CD2 X anti-tumor-associated antigen antibody and/or anti-CD5 X anti-tumor-associated antigen antibody and/or anti-CD28 X anti-tumor-associated antigen antibody and/or anti-CD44 X anti-tumor-associated antigen antibody having an additional anti-Fc receptor binding arm.

Preferred antibodies are heterologous trifunctional bispecific antibodies, preferably monoclonal, selected from one or more of the following combinations of isotypes:
- rat-IgG2b/mouse-IgG2a,
- rat-IgG2b/mouse-IgG2b,
- rat-IgG2b/mouse-IgG3;
- rat-IgG2b/human-IgG1,
- rat-IgG2b/human-IgG2
- rat-IgG2b/human-IgG3 [oriental allotype G3m(st)=binding to protein A], rat-IgG2b/human-IgG4;
- rat-IgG2b/rat-IgG2c;
- mouse-IgG2a/human-IgG3 [caucasian allotypes G3m(b+g)=no binding to protein A, in the following indicated as *]
- mouse-IgG2a/mouse-[VH-CH1, VL-CL]-human-IgG1-[hinge]-human-IgG3*-[CH2-CH3]
- mouse-IgG2a/rat-[VH-CH1, VL-CL]-human-IgG1-[hinge]-human-IgG3*-[CH2-CH3]
- mouse-IgG2a/human-[VH-CH1, VL-CL]-human-IgG1-[hinge]-human-IgG3*-[CH2-CH3]
- mouse-[VH-CH1, VL-CL]-human-IgG1/rat-[VH-CH1, VL-CL]-human-IgG1-[hinge]-human-IgG3*-[CH2-CH3]
- mouse-[VH-CH1, VL-CL]-human-IgG4/rat-[VH-CH1, VL-CL]-human-IgG4-[hinge]-human-IgG4 [N-terminal region of CH2]-human-IgG3*[C-terminal region of CH2:>aa position 251]-human-IgG3*[CH3]
- rat-IgG2b/mouse-[VH-CH1, VL-CL]-human-IgG1-[hinge-CH2-CH3]
- rat-IgG2b/mouse-[VH-CH1, VL-CL]-human-IgG2-[hinge-CH2-CH3]
- rat-IgG2b/mouse-[VH-CH1, VL-CL]-human-IgG3-[hinge-CH2-CH3, oriental allotype]
- rat-IgG2b/mouse-[VH-CH1, VL-CL]-human-IgG4-[hinge-CH2-CH3]
- human-IgG1/human-[VH-CH1, VL-CL]-human-IgG1-[hinge]-human-IgG3*-[CH2-CH3]
- human-IgG1/rat-[VH-CH1, VL-CL]-human-IgG1-[hinge]-human-IgG4 [N-terminal region of CH2]-human-IgG3*[C-terminal region of CH2:>aa position 251]-human-IgG3*[CH3]
- human-IgG1/mouse-[VH-CH1, VL-CL]-human-IgG1-[hinge]-human-IgG4 [N-terminal region of CH2]-human-IgG3*[C-terminal region of CH2:>aa position 251]-human-IgG3*[CH3]
- human-IgG1/rat-[VH-CH1, VL-CL]-human-IgG1-[hinge]-human-IgG2 [N-terminal region of CH2]-human-IgG3*[C-terminal region of CH2:>aa position 251]-human-IgG3*[CH3]
- human-IgG1/mouse-[VH-CH1, VL-CL]-human-IgG1-[hinge]-human-IgG2 [N-terminal region of CH2]-human-IgG3*[C-terminal region of CH2:>aa position 251]-human-IgG3*[CH3]
- human-IgG1/rat-[VH-CH1, VL-CL]-human-IgG1-[hinge]-human-IgG3*-[CH2-CH3]
- human-IgG1/mouse-[VH-CH1, VL-CL]-human-IgG1-[hinge]-human-IgG3*-[CH2-CH3]
- human-IgG2/human-[VH-CH1, VL-CL]-human-IgG2-[hinge]-human-IgG3*-[CH2-CH3]
- human-IgG4/human-[VH-CH1, VL-CL]-human-IgG4-[hinge]-human-IgG3*-[CH2-CH3]
- human-IgG4/human-[VH-CH1, VL-CL]-human-IgG4-[hinge]-human-IgG4 [N-terminal region of CH2]-human-IgG3*[C-terminal region of CH2:>aa position 251]-human-IgG3*[CH3]

mouse-IgG2b/rat-[VH-CH1, VL-CL]-human-IgG1-[hinge]-human-IgG3*-[CH2-CH3]
mouse-IgG2b/human-[VH-CH1, VL-CL]-human-IgG1-[hinge]-human-IgG3*-[CH2-CH3]
mouse-IgG2b/mouse-[VH-CH1, VL-CL]-human-IgG1-[hinge]-human-IgG3*-[CH2-CH3]

Specifically preferred are the following antibodies:
A trifunctional bispecific antibody with monovalent binding specificities comprising the following properties:
a) binding to a T cell;
b) binding to a tumor-associated antigen on a tumor cell;
c) binding via its Fc-portion to an Fc-receptor positive cell,
and wherein the trifunctional bispecific antibody is further preferably selected of a group of antibodies with the following isotype combinations:
rat-IgG2b/mouse-IgG2a,
rat-IgG2b/mouse-IgG2b,
rat-IgG2b/human-IgG1,
mouse-[VH-CH1; VL-CL]-human-IgG1/rat-[VH-CH1, VL-CL]-human-IgG1-[hinge]-human-IgG3*-[CH2-CH3]
[*=Caucasian allotypes G3m(b+g)=no binding to protein A].

Specifically preferred is an antibody, preferably a trifunctional bispecific antibody and/or a scaffold protein directed against EpCAM and CD3 with the isotype combination rat-IgG2b/mouse-IgG2a. A preferred example for said trifunctional bispecific antibody is catumaxomab. Preferably said antibody is monoclonal.

Preferably, the antibodies according to the invention are monoclonal, chimeric, recombinant, synthetic, semi-synthetic, or chemically modified intact antibodies having for example Fv, Fab, scFv, or F (ab)2 fragments.

In the method of the present invention also antibodies or derivatives or fragments of human origin can be used, or antibodies modified to be suitable for the use in humans (so-called "humanized antibodies") (see for example Shalaby et al., J. Exp. Med. 175 (1992), 217; Mocikat et al., Transplantation 57 (1994), 405).

The preparation of the different types of antibodies and antibody fragments mentioned above is obvious to the skilled artisan. The preparation of monoclonal antibodies preferably of mammalian origin, e.g. of human, rat, mouse, rabbit, or goat, can be performed using conventional methods for example as those described in Köhler and Milstein (Nature 256 (1975), 495), in Harlow and Lane (Antibodies, A Laboratory Manual (1988), Cold Spring Harbor) or in Galfré (Meth. Enzymol. 73 (1981), 3).

It is further possible to prepare the antibodies described by means of recombinant DNA technology according to techniques obvious to the skilled artisan (see Kurucz et al., J. Immunol. 154 (1995), 4576; Hollinger et al., Proc. Natl. Acad. Sci. USA 90 (1993), 6444).

The preparation of antibodies having two different specificities, the so-called bispecific antibodies, can be performed for example using recombinant DNA technology but also by the so-called hybrid hybridoma fusion technique (see for example Milstein et al., Nature 305 (1983), 537). This technique consists of fusing hybridoma cell lines each producing antibodies having one of the desired specificities and identifying and isolating recombinant cell lines producing antibodies having both specificities.

The problem forming the basis of the invention can be overcome by using in preferred embodiments either trifunctional bispecific or trispecific trifunctional antibodies if they exhibit the properties and effects as described herein. The invention is particularly described by the way of trifunctional bispecific antibodies. However, it is understood that it also covers the following trispecific antibodies exhibiting similar effects.

The preparation of antibodies exhibiting three specificities, so-called trispecific antibodies, also suitable to solve the basic problem of the invention may for example be carried out by coupling a third antigen binding site having an additional specificity, e.g. in the form of "single chain variable fragments" (scFv) to one of the IgG heavy chains of a bispecific antibody. The scFv may be coupled for example using a-S-S(G4S)nD-I (SEQ ID NO:1) linker to one of the heavy chains (S=serine, G=glycine, D=aspartate, I=isoleucine).

Analogously, trispecific F(ab)2 constructs may be prepared by replacing the CH2-CH3 regions of the heavy chain of one specificity of a bispecific antibody by an scFv having a third specificity, while the CH2-CH3 regions of the heavy chain having the other specificity can be removed for example by insertion of a stop codon (at the end of the "hinge" 5 region) into the coding gene, e.g by homologous recombination.

It is also possible to prepare trispecific scFv constructs wherein three VH-VL regions representing three different specificities are arranged in series.

According to the invention there are intact bispecific antibodies used. Intact bispecific antibodies are composed of two antibody semi-molecules (each having a H and a L immunoglobulin chain) each representing a specificity, and additionally like normal antibodies having a Fc portion performing the well-known effector functions. They are preferably prepared using the quadroma technology. This method of preparation is exemplified in DE-A-44 19 399. For complete disclosure this document is incorporated in its entirety by reference also with respect to a definition of bispecific antibodies. It should be understood that other methods of preparation are also useful if they lead to the intact bispecific antibodies according to the above definition required according to the invention.

For example, intact bispecific antibodies may be produced in sufficient amounts using a newly developed method of preparation (Lindhofer et al., J. Immunology, 155:219 (1995)). The combination of two bispecific antibodies directed against two different tumor-associated antigens (e.g. c-erb-B2, EpCAM, such as GA-733-2=C215) on the mammary carcinoma cells minimizes the risk that tumor cells expressing only one of the antigens remain unidentified.

In accordance with the method of the present invention, the antibodies or the scaffold proteins recognizing the tumor-associated antigens on a tumor cell are not bound to or by any means like magnetic particles or magnetic beads which might have been used in the art as a tool in order to remove associates which are formed via the binding of said antibodies to said tumor cells and optionally immune cells. Further, the prior art describes the labeling of the tumor cells or the antibodies with e.g. chromogenic substances like fluorochromes followed by cell sorting like flow cytometry. Contrary thereto, the principle of the invention lies in the formation of three dimensional networks (associates) as described above of a size sufficient to be retained by filters or to be separated by centrifugal forces and the direct removal of said networks by mechanical means like filtration or centrifugation or a combination thereof. The size of the associates formed by interaction with the antibodies is in a magnitude to be removable by filtration or centrifugation. Embodiments with magnetic beads or similar tools which bind to the antibodies or the tumor cells as indirect auxiliary means to remove the associates between the antibodies and the tumor cells are excluded from the present invention. Also separation methods like flow cytometric methods wherein tumor cells are separated from normal cells are excluded from the invention.

Contacting the Antibody and/or the Scaffold Protein with IBS

Provided that any of the antibodies is not able to bind to immune cells but only to identical or different tumor-associated antigens, it is of crucial importance that there is a cross-linkage between at least two different tumor cells in order to obtain associates between the antibody and at least two tumor cells.

The terms "associates", "multi-cellular complexes" and "aggregates" are used interchangeably and always define a three-dimensional network between antibodies, tumor cells and/or immune cells and/or further tumor cells in order to form cross-linked tumor cells which are removable by centrifugation or filtration or a combination thereof. Said associates are specifically comprised of a) antibodies, tumor cells and immune cells and/or
b) antibodies and tumor cells, and/or
c) scaffold proteins, tumor cells and immune cells and/or
d) scaffold proteins and tumor-cells.

The at least one antibody and/or the at least one scaffold protein are contacted with said intra-operatively obtained blood salvage for a time period which is sufficient to cross-link tumor cells and optionally immune cells and/or other tumor cells in order to obtain associates. Said tumor cells and said immune cells are potentially present in said intra-operatively obtained blood salvage. Said tumor cells are specifically recognized by said at least one antibody or said at least one scaffold protein.

The time period which is necessary to achieve said cross-linkage can be determined by a person skilled in the art with routine methods. Generally a contact period is between 10 and 118 minutes, preferably between 20 and 90 minutes and further preferably between 30 and 60 minutes. The temperature is preferably room temperature which might range from 19° C. to 25° C., preferably about 21° C.

The amount of antibodies and/or scaffold proteins which have to be applied in order to obtain said associates comprising antibodies and/or scaffold proteins mimicking antibodies may be determined by a person skilled in the art by routine measurements. The amount of antibody and/or scaffold protein to be applied is generally dependent on the binding affinity of the antibody and/or scaffold protein to said tumor antigen. Further amounts are 1 µg to 20 µg per liter IBS, further preferred 1 µg to 10 µg per liter IBS, 1 µg to 5 µg per liter IBS or 1 µg to 2 µg per liter IBS.

In order to optimize said method, at least two different antibodies and/or scaffold proteins are applied which tumor antigen specificity or T cell surface marker specificity differs from each other.

Removal of Tumor Cell and Antibody/Scaffold Protein Associates from IBS

The associates are removed finally from said intra-operatively obtained blood salvage (IBS) in order to obtain an IBS which is essentially free of tumor cells. Depletion of said cell aggregates is preferably achieved by centrifugation, by filtration or a combination thereof. In a preferred method, at least one centrifugation step and preferably further at least one filtration step are included.

The filtration is generally a leukocyte reduction or depletion filtration wherein all leukocytes contaminated by said tumor cells are removed while the erythrocytes pass the filter and are collected. The filters might be selected from screen filters with pore sizes of between 20 µm to 40 µm which retain the associates formed by the method of the invention and also for instance fibrin strands and clumps of dead cells. Erythrocytes which are about 8 µm in size can pass through the filters. Micro aggregate filters are typically used for the re-infusion of shed autologous blood collected during or after surgery. In order to receive leukocyte reduced red blood cells, filtration through a standard blood administration filter with a pore size of between 170 µm to 260 µm would be used.

A review describing the cell saver devices including separation methods is Carless P A, Henry D A, Moxey A J, O'Connell D, Brown T, Fergusson D A, Cell salvage for minimizing perioperative allogeneic blood transfusion, 2010, The Cochrane Collaboration, John Wiley & Sons, Ltd. which is fully incorporated by reference.

An example for a micro-aggregate blood filter in order to receive an erythrocyte containing fraction only is Pall SQ 40S Blood Transfusion Filter.

Centrifugation is performed generally by a density gradient centrifugation step followed by washing with physiological saline for a time and with a rotational speed sufficient to remove said tumor cells-comprising associates and to separate erythrocytes from said tumor cell associates and optionally from leukocytes.

Filtration is performed generally for a time period sufficient to remove said tumor cells-comprising associates and to separate erythrocytes from said tumor cell associates and optionally from leukocytes.

In a preferred embodiment said concentrate of erythrocytes free of contaminating tumor cells is used without addition of physiological saline.

Further filtration steps may be used in order to remove residual associates and/or leukocytes.

As the underlying leukocyte filtration technology is different from classical, micron-rated filtration procedures including clogging issues, this advanced tumor cell removal strategy appears to be feasible.

It is one of the benefits of the invention that the time involved for said removal of tumor cells is dramatically reduced by the invention compared to the depletion of tumor cells by destruction with antibodies or by removal with magnetic beads or cell sorting methods.

The blood products obtained by using the method of the invention are then re-administered into the patient from whom the starting blood sample was obtained.

EXAMPLES

Anti-EpCAM Mediated Removal of Tumor Cells Through Multicell Complex Depletion by Centrifugation and/or Filtration During IBS Expression profiles of the transmembrane glycoprotein EpCAM classified by tissue microarray staining occurs in carcinomas of various tumors (Table. 3). This broad expression EpCAM pattern represents an interesting hallmark of carcinomas which may be not only considerable for therapeutical application but also for improved IBS protocols during cancer surgeries. Nevertheless, it should be noted that most soft-tissue tumors and all lymphomas were completely EpCAM negative.

TABLE 3

Tissue microarray: EpCAM expression profile on various tumor entities

| Tumor Entity | Number of samples (n) | Negative Expression (%) | Weak/Moderate Expression# (%) | Strong Expression* (%) |
|---|---|---|---|---|
| Prostate[1] | 414 | 1.9 | 10.9 | 87.2 |
| Colon[1] | 1186 | 0.3 | 1.9 | 97.7 |
| Lung[1] | 1287 | 13.5 | 22.5 | 63.9 |
| Gastric[1] | 473 | 2.5 | 6.8 | 90.7 |
| Ovarian[2] | 272 | 2.6 | 12.1 | 85.3 |

[1]Data taken from Went et al., *Brit. J. Cancer* 94: 128, 2006.
[2]Data taken from Spizzo et al., *Gyneological Oncology* 103: 483, 2006.
Score 1-4; EpCAM-expression was defined by calculating of total staining score as the product of a proportion score (0-4) and an intensity score (0-3). The proportion score described the estimated fraction of positive stained tumor cells (0, none; 1, <10%; 2, 10-50%; 3, 50-80%; 4, >80%) . The intensity score represented the estimated staining intensity (0, no staining; 1, weak; 2, moderate; 3, strong).
*Score >4; the total expression score ranged from 0 to 12, thus EpCAM overexpression was defined as a total score >4.

Figure 1:
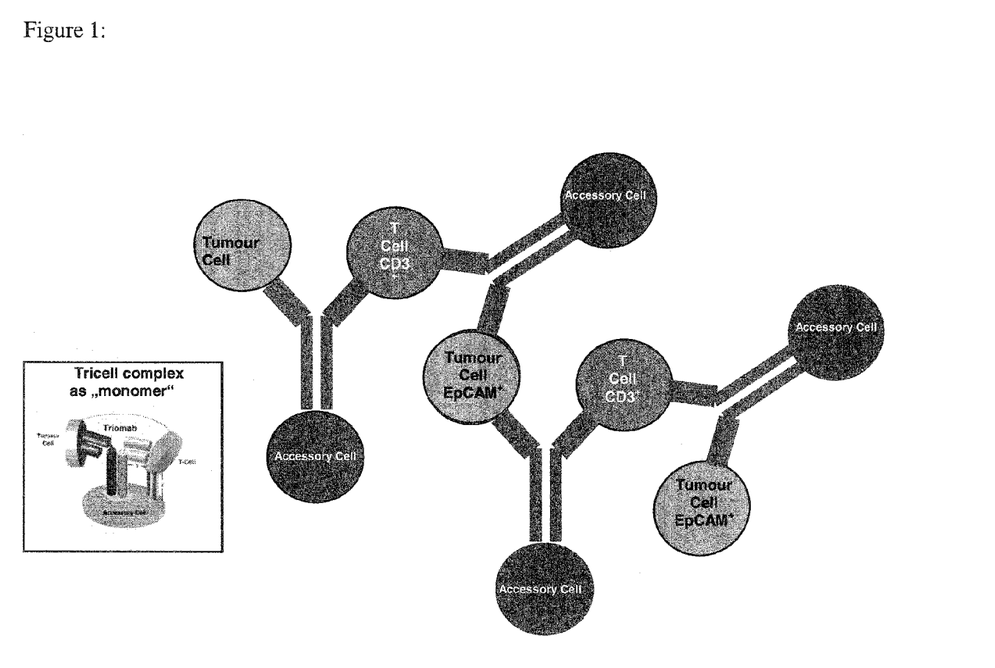
FIG. 1: The principle of formation of large multicell complexes—induced by trifunctional antibodies—is shown. Said complex formation allows tumor cell removal by intraoperative blood sample device-specific processing steps (e.g. centrifugation)

3.1. Calculations for the In Vitro Application of Anti-EpCAM Catumaxomab During IBS Our research hypothesis is that the tumor cells—present in catumaxomab-mediated large multicell complexes (see FIGS. 1 and 2)—may be efficiently removed by centrifugation and/or leukocyte filters (e.g. RC400 or other state-of-the-art leukocyte depletion filters from Pall) in contrast to tumor cells that only float in single cell suspensions prior filtration.

Based on the following calculations we will give specifications for the catumaxomab-mediated formation of large cell complexes. One liter of intraoperative collected blood (peripheral blood) contains about $5 \times 10^{12}$ erythrocytes, $5 \times 10^9$ leukocytes (including a proportion of 34% lymphocytes with approximately 80% CD3+ T cells) (Hansen, *TATM* 2: 472, 2003; Labor and Diagnose edited by L. Thomas, TH-Books Verlagsgesellschaft mbh, Frankfurt/Main, 2000). Thus, young adults have about $1.3 \times 10^9$ CD3+ T cells per liter peripheral blood or IBS. This IBS blood volume from cancer surgery could also contain residual tumor cells ranging from 10 up to $10^7$. Assuming that one T cell displays about $10^5$ CD3 molecules at its surface (Ginaldi et al. *Br. J. Haematol.* 93: 921, 1996) and that only 3% of CD3 molecules are sufficient for the anti-CD3 catumaxomab-mediated retargeting of T cells to tumor cells, thus at least 1 μg (representing $10^{12}$ molecules) of the trifunctional bispecific anti-EpCAM/anti-CD3 antibody catumaxomab would be required to quantitatively bind to $1.3 \times 10^9$ T cells. According to these calculations 1-5 μg of catumaxomab should be used per 1 liter of IBS sample for the formation of large cell complexes consisting of $10^7$ (up to $10^8$ tumor cells based on safety considerations) EpCAM-expressing tumor cells linked to about $10^9$ CD3 T cells. In addition, at a similar ratio catumaxomab would also interact with Fcgamma-receptor type I, IIa and type III of accessory cells like macrophages, NK cells and monocytes which may enlarge these multi-cellular complexes even more.

In summary, the catumaxomab concentration of 1-5 μg per liter IBS would secure the formation of large cell complexes containing up to $10^8$ tumor cells.

It should be noted that leukocyte reduction filters are not micron rated but rather classified by their efficiency to reduce leukocytes. Filtration is mainly based on a number of mechanisms, including adsorption of the leukocytes to the filtration media. The efficiency claims for Pall Purecell® High Efficiency Leukocyte Reduction filters are based on performance data using average leukocyte residual counts (see Appendix). In contrast, the Pall SQ40S microaggregate filters for blood transfusion are 40 micron rated. Pall microaggregate filters are a screen type filter, and filtration is based on direct interception to retain particles and microaggregates. Pall microaggregate filters are indicated for the transfusion of stored blood, packed red cells, platelet and an organ flushing and storage solution. Although Pall SQ40S filters retain microaggregates that consist of nonviable leukocytes, they do not achieve the low residual levels possible with Pall leukocyte reduction filters (see Appendix).

To analyse the tumor cell removal capacity of a combined catumaxomab/leukocyte depletion approach during IBS with an automatic device (e.g. Cell Saver-5®) the following experiments were performed:

Patient 1:

1500 ml patient's blood were collected with addition of anti-coagulants during surgery. 100 ml of the 1500 ml blood were taken and sent to the laboratory (sample 1: Blood). 400 ml of the remaining 1400 ml were then centrifuged with the cell saver machine and the emerging erythrocyte concentrate (EC) was sent to the laboratory (sample 2: EC). The remaining 1000 ml blood was incubated for 1 h with 2 μg catumaxomab. After incubation 500 ml blood were again centrifuged in the cell saver machine and the emerging erythrocyte concentrate was sent to the laboratory (sample 3: EC+antibody). The remaining 500 ml were also centrifuged with the cell saver system, purified with a leucocyte filter and the EC was sent to the laboratory (sample 4: EC+antibody+Filter).

The laboratory analyzed the 4 samples for tumor cell count, cytokine secretion and free catumaxomab antibody. Nuclear cells were won by density centrifugation and/or lysis of erythrocytes. Supernatants were sampled for analysis of cytokine secretion and free catumaxomab measurements. Cells were transferred to cytospin slides (2.5×10e5 cells per slide) and 6 slides were stained with the anti EpCAM antibody VU1D9 recognizing a different epitope than catumaxomab to eliminate potential blocking or masking effects. After staining tumor cells were counted by a computerized image analysis system and reviewed by a qualified operator. Cytokines were measured by Luminex technology and free catumaxomab levels were determined by sensitive ELISA technique. Table 1-3 shows the results of patient 1:

TABLE 1

Tumor cell count:

| Tumor cell count | Sample 1: Blood | Sample 2: EC | Sample 3: EC + antibody | Sample 4: EC + antibody + Filter |
|---|---|---|---|---|
| | 5.2 × 10e2 | 40 | 0 | 0 |

All results are extrapolated to the original blood volumes; EC: erythrocyte concentrate

TABLE 2

Cytokine secretion

| Cytokine secretion pg/ml | Sample 1: Blood | Sample 2: EC | Sample 3: EC + antibody | Sample 4: EC + antibody + Filter |
|---|---|---|---|---|
| | IL10: 46; IL2: BLQ; IL4: BLQ; | IL10: BLQ; IL2: BLQ; IL4: BLQ; IL6: | IL10: 4; IL2: BLQ; IL4: 10; IL6: | n.d. |

TABLE 2-continued

Cytokine secretion

| Cytokine secretion pg/ml | Sample 1: Blood | Sample 2: EC | Sample 3: EC + antibody | Sample 4: EC + antibody + Filter |
|---|---|---|---|---|
| | IL6: 1003; IL8: 189; IFNg: BLQ; TNFa: 5 | 119; IL8: 43; IFNg: BLQ; TNFa: 3 | 114; IL8: 48; IFNg: BLQ; TNFa: 4 | |

EC: erythrocyte concentrate; limit of quantification 3 pg/ml

TABLE 3

Free catumaxomab

| Free catumaxomab in pg/ml | Sample 1: Blood | Sample 2: EC | Sample 3: EC + antibody | Sample 4: EC + antibody + Filter |
|---|---|---|---|---|
| | BLQ | BLQ | BLQ | BLQ |

EC: erythrocyte concentrate; BLQ: below limit of quantification; limit of quantification: 250 pg/ml Patient 2

1100 ml patient's blood were collected with addition of anti-coagulants during surgery. 100 ml of the 1100 ml blood were taken and sent to the laboratory (sample 1: Blood). The remaining 1000 ml blood was incubated for 1 h with 2 µg catumaxomab. After incubation 100 ml blood were taken and sent to the laboratory (sample 2: Blood+antibody). The remaining 900 ml blood were then centrifuged in the cell saver system and the emerging erythrocyte concentrate was sent to the laboratory (sample 3: EC+antibody).

The laboratory analyzed the 3 samples for tumor cell count, cytokine secretion and free catumaxomab antibody. Nuclear cells were won by density centrifugation and/or lysis of erythrocytes. Supernatants were sampled for analysis of cytokine secretion and free catumaxomab measurements. Cells were transferred to cytospin slides (2.5×10e5 cells per slide) and 6 slides were stained with the anti EpCAM antibody VU1D9 recognizing a different epitope than catumaxomab to eliminate potential blocking or masking effects. After staining tumor cells were counted by a computerized image analysis system and reviewed by a qualified operator. Cytokines were measured by Luminex technology and free catumaxomab levels were determined by sensitive ELISA technique. Table 1-3 shows the results of patient 2:

TABLE 1

Tumor cell count:

| Tumor cell count | Sample 1: Blood | Sample 2: Blood + antibody | Sample 3: EC + antibody |
|---|---|---|---|
| | 2.8 × 10e3 | 2.0 × 10e3 | 0 |

All results are extrapolated to the original blood volumes; EC: erythrocyte concentrate

TABLE 2

Cytokine secretion

| Cytokine secretion pg/ml | Sample 1: Blood | Sample 2: Blood + antibody | Sample 3: EC + antibody |
|---|---|---|---|
| | IL10: 41; IL2: BLQ; IL4: BLQ; IL6: 1011; IL8: 347; IFNg: 9; TNFa: 4 | IL10: 145; IL2: BLQ; IL4: BLQ; IL6: 5464; IL8: 295; IFNg: 17; TNFa: 6 | IL10: 5; IL2: BLQ; IL4: 10; IL6: 152; IL8: 42; IFNg: BLQ; TNFa: BLQ |

EC: erythrocyte concentrate; IL:Interleukin; IFN: Interferone; TNF: Tumor necrosis factor; limit of quantification 3 pg/ml

TABLE 3

Free catumaxomab

| Free catumaxomab in pg/ml | Sample 1: Blood | Sample 2: Blood + antibody | Sample 3: EC + antibody |
|---|---|---|---|
| | BLQ | 289 | BLQ |

EC: erythrocyte concentrate; BLQ: below limit of quantification; limit of quantification: 250 pg/ml

SUMMARY

Both blood samples of cancer patients purified with the cell saver system and catumaxomab showed no detectable remaining tumor cells (0) in the erythrocyte concentrates. Furthermore, cytokines which are secreted during surgery are clearly decreased in the erythrocyte concentrate after the described procedure, revealing no safety issues for the patient. Importantly, residual catumaxomab could not be detected in the produced erythrocyte concentrates even with a very sensitive ELISA method (detection limit: 250 pg/ml) confirming the safety for potential patients receiving these purified autologous erythrocyte concentrates.

CONCLUSIONS

Due to infection and other risks through allogeneic blood transfusions, increasing demands and economical needs intraoperative blood salvage gains more interest in blood management programs of hospitals. Nevertheless, the use of intraoperative autotransfusion in major cancer surgeries has been limited due to the probability that tumor cells would be reinfused into the patient thus leading to augmented incidences of recurrence.

It has been found that the EpCAM-specific antibody catumaxomab with its binding capacity to carcinoma cells, T cells and accessory cells mediates the formation of large multi-cellular complexes that could be simply removed by centrifugation and/or leukocyte filtration, conventional steps for leukocyte removal. The invention shows the catumaxomab-mediated tumor cell/leukocyte removal capability during intraoperative blood salvage by using e.g. automatic devices like Cell Saver-5® or CATS®. The in vitro application of catumaxomab represents besides its therapeutic use a secondary use as medical device and medical product, respectively, during the intraoperative blood salvage process in cancer surgery.

Starting with these experimentally supported data, it is evident for a person skilled in the art that this experimentally proved concept can also be transferred effectively to other monoclonal antibodies provided that they are able to interact with tumor cells and optionally with immune cells and/or other tumor cells in order to form aggregates or associates which can be removed by e.g. filtration or centrifugation. For these reasons, the present invention is not limited to trifunctional bispecific antibodies like catumaxomab which recognizes the tumor-associated antigen EpCAM and T cells via CD3 and the specific isotype combinations presented herein; having described herein the concept of the present invention, it can easily be transferred to other antibodies and tumor-associated antigens as described herein as long as they are able to recognize tumor-associated antigens and have the ability to form removable associates.

Taken together, the application of the method of the present invention, e.g. by using catumaxomab to minimize the risk of residual autologous tumor cells would be a prerequisite to perform IBS during cancer surgery.

Blood Transfusion Filters for the Hospital Bedside/Laboratory (www.pall.com/medical_6595.asp)

| Product(s) | Indication | Performance (residual leukocytes/unit) |
|---|---|---|
| Red Cell Purecell ® RCEZ (gravity prime), Purecell RCQ (gravity prime/rapid flow setting), Purecell RCXL1 | Bedside filtration of one unit of packed red blood cells or whole blood | Consistently averaging $<2 \times 10^5$ |
| Purecell RCXL2 | Bedside filtration of two units of packed red blood cells or one unit of whole blood | Consistently averaging $<2 \times 10^5$ |
| Platelet Purecell ® PXLA | Filtration of a single unit of apheresis platelets produced on systems using protocols designed to produce an initial level of leukocyte reduction | Consistently averaging $<3 \times 10^4$ |
| Purecell PL6 (gravity prime) | Bedside filtration of a pool of up to 6 random donor platelets or standard apheresis unit | Consistently averaging $<5 \times 10^5$ |
| Purecell PXL8 | Bedside filtration of a pool of 3 to 8 random donor platelets or standard apheresis unit | Consistently averaging $<5 \times 10^5$ |
| Purecell PXL12 | Bedside filtration of a pool of 8 to 12 random donor platelets or standard apheresis unit | Consistently averaging $<5 \times 10^5$ Consistently averaging $<4 \times 10^4$ |
| Plasma Purecell LPS2 | Filtration of up to 1600 mL of fresh frozen plasma | |
| Microaggregate Filter Pall SQ40S Microaggregate Blood Transfusion Filter | For the transfusion of whole blood, packed red blood cells, platelet and granulocyte concentrations and filtration of ViaSpan ® Cold Storage Solution (ViaSpan is a registered trademark of DuPont Merck Pharmaceutical Co.) | Not applicable |
| Pediatric/Neonatal Transfusion Purecell NEO | Filtration of an aliquot of up to 60 mL of packed red blood cells | Consistently averaging $<2 \times 10^5$ |
| Purecell PL1 | Filtration of one unit of platelet concentrate derived from a unit of whole blood | Consistently averaging $<4.5 \times 10^4$ |
| Hospital Laboratory Filtration Purecell BPF (gravity prime) | Laboratory filtration of one unit of packed red blood cells or whole blood | Consistently averaging $<5 \times 10^4$ |
| Purecell LRF | Laboratory filtration of a pool of up to 6 random donor platelet concentrates or standard apheresis unit | Consistently averaging: $<5 \times 10^5$ (platelet pool) $<2 \times 10^5$ (standard apheresis unit) |
| Pall LRF10 | Laboratory filtration of a pool of up to 10 random donor platelet concentrates or standard apheresis unit | Consistently averaging $<5 \times 10^5$ |

The invention claimed is:

1. An ex vivo method for removal of tumor cells from blood of a tumor patient, the method comprising:
   providing blood suspected of containing tumor cells intra-operatively salvaged from a tumor patient;
   contacting the intra-operatively salvaged blood for a time period of between 10 and 180 minutes with a cross-linking agent capable of forming a three-dimensional network comprising the tumor cells, wherein the cross-linking agent comprises:
      at least one antibody selected from the group consisting of a bispecific antibody, a trispecific antibody, a tetraspecific antibody, a multispecific antibody, a bivalent antibody, a trivalent antibody, a tetravalent antibody, and a multivalent antibody, or
      at least one scaffold protein with multispecific or multivalent binding properties similar to antibodies, or
      a combination thereof, wherein the at least one antibody, the at least one scaffold protein, or the combination thereof specifically binds to at least one epitope of the tumor cells to thereby crosslink the tumor cells,
   and further wherein the time period of between 10 and 180 minutes is sufficient to form associates by cross-linking tumor cells present in the intra-operatively salvaged blood with the at least one antibody, the at least one scaffold protein, or the combination thereof of a size sufficient to be retained by filtration or to be separated by centrifugation, optionally wherein the associates further comprise cross-linked immune cells and/or other tumor cells;
   mechanically removing the associates from the intra-operatively salvaged blood; and
   readministering the intra-operatively salvaged blood to the patient after mechanically removing the associates.

2. The ex vivo method according to claim 1, wherein the tumor cells comprise epithelial tumor cells, haematological tumor cells, or neuroectodermal tumor cells.

3. The ex vivo method according to claim 1, wherein the at least one antibody comprises a trifunctional bispecific antibody comprising the following properties:
   a) binding to a T cell;
   b) binding to a tumor-associated antigen on a tumor cell;
   c) binding via its Fc-portion to an Fc-receptor positive cell,
and wherein the trifunctional bispecific antibody is selected from among the following isotype combinations:
   rat-IgG2b/mouse-IgG2a,
   rat-IgG2b/mouse-IgG2b,
   rat-IgG2b/human-IgG1,
   mouse-[VH-CH1; VL-CL]-human-IgG 1/rat-[VH-CH1, VL-CL]-human-IgG1-[hinge]human-IgG3*-[CH2-CH3]
   [*=Caucasian allotypes G3m(b+g)=no binding to protein A].

4. The ex vivo method according to claim 3, wherein the Fc-receptor positive cell is selected from the group consisting of an Fc-gamma receptor I-positive accessory cell, an Fc-gamma receptor IIa-positive accessory cell, and an Fc-gamma receptor III-positive accessory cell.

5. The ex vivo method according to claim 4, wherein the Fc-receptor positive cells are selected from the group consisting of a monocyte, a macrophage, a dendritic cell, a natural killer cell, a neutrophil, and an eosinophil.

6. The ex vivo method according to claim 3, wherein the tumor associated antigen is selected from the group consisting of EpCAM, Her2/neu, EGFR, CD30, CD20, CD22, MUC1, MUC1*, PSMA, CD33, MCSP, cMet, EphA2, endosialin, carboanhydrase IX, IGF-1R, FAP-alpha, CD19, CD52, GD2, CEA, FR, a proteoglycan, G250, GC182, GT468, and GT512.

7. The ex vivo method according to claim 3, wherein the trifunctional bispecific antibody recognizes a surface marker of T cells selected from the group consisting of CD3, CD2, CD4, CD5, CD6, CD6, CD8 and CD28.

8. The ex vivo method according to claim 1, further comprising at least two different antibodies and/or scaffold proteins comprising different tumor antigen specificities or different T cell surface marker specificities are employed.

9. The ex vivo method according to claim 1, wherein the associates comprise:
   a) antibodies, tumor cells, and immune cells; and/or
   b) antibodies and tumor cells; and/or
   c) scaffold proteins, tumor cells, and immune cells; and/or
   d) scaffold proteins and tumor cells.

10. The ex vivo method according to claim 1, wherein the at least one antibody and/or the at least one scaffold protein is applied in an amount selected from the group consisting of 1 µg to 20 µg, 1 µg to 10 µg, 1 µg to 5 µg, and 1 µg to 2 µg per liter of intra-operatively salvaged blood.

11. The ex vivo method according to claim 1, wherein the at least one antibody and/or the at least one scaffold protein is directed against EpCAM and CD3.

12. The ex vivo method according to claim 1, wherein the method further comprises at least one of the following additional steps:
   mixing the intra-operatively salvaged blood before addition of the at least one antibody and/or the at least one scaffold protein with at least one anticoagulating agent to obtain a mixture, and optionally filtering the mixture to remove potentially residual associates and residual cell complexes; and/or
   separating erythrocytes from the associates and further blood components via separate containers.

13. The ex vivo method according to claim 1, wherein the contacting step of the at least one antibody and/or the at least one scaffold protein with said intra-operatively salvaged blood is for an incubation time selected from the group consisting of between 20 and 90 minutes and between 30 and 60 minutes, and optionally wherein centrifugation, further optionally density gradient centrifugation, is employed to obtain an erythrocyte-containing fraction; and/or
   collecting the erythrocyte-containing fraction and further blood components in the contacting step is performed at a temperature of between 19 to 25° C., optionally at room temperature.

14. The ex vivo method according to claim 1, wherein the step of removing the associates is by centrifugation, filtration, or a combination thereof.

15. The ex vivo method according to claim 1, further comprising removing leukocytes and/or tumor cell-containing cell complexes using a leukocyte adsorption filter.

* * * * *